(12) United States Patent
Wubbeling et al.

(10) Patent No.: US 9,801,745 B2
(45) Date of Patent: Oct. 31, 2017

(54) SYSTEM TO DELIVER A BODILY IMPLANT

(75) Inventors: Martin Wubbeling, Mannheim (DE); Daniel Dietrich, Karlsruhe (DE)

(73) Assignee: C.R. Bard, Inc., Murray Hill, NJ (US)

( * ) Notice: Subject to any disclaimer, the term of this patent is extended or adjusted under 35 U.S.C. 154(b) by 518 days.

(21) Appl. No.: 13/878,187

(22) PCT Filed: Oct. 19, 2011

(86) PCT No.: PCT/EP2011/068238
§ 371 (c)(1),
(2), (4) Date: Apr. 5, 2013

(87) PCT Pub. No.: WO2012/052469
PCT Pub. Date: Apr. 26, 2012

(65) Prior Publication Data
US 2013/0211493 A1    Aug. 15, 2013

Related U.S. Application Data

(60) Provisional application No. 61/405,514, filed on Oct. 21, 2010.

(30) Foreign Application Priority Data

Oct. 21, 2010 (GB) .................................. 1017834.1

(51) Int. Cl.
*A61F 2/95* (2013.01)
*A61F 2/966* (2013.01)

(52) U.S. Cl.
CPC ................ *A61F 2/95* (2013.01); *A61F 2/966* (2013.01); *A61F 2002/9517* (2013.01)

(58) Field of Classification Search
CPC .. A61F 2/95; A61F 2/958; A61F 2/966; A61F 2002/9665; A61F 2002/9505;
(Continued)

(56) References Cited

U.S. PATENT DOCUMENTS

| 1,988,060 A | 1/1935 | Vollenbroich |
| 2,934,211 A | 4/1960 | Shivek |

(Continued)

FOREIGN PATENT DOCUMENTS

| CA | 2155527 A1 | 8/1994 |
| DE | 1775056 A1 | 3/1972 |

(Continued)

OTHER PUBLICATIONS

U.S. Appl. No. 11/652,737, filed Jan. 12, 2007 Non-Final Office Action dated Nov. 12, 2008.
(Continued)

*Primary Examiner* — Eric Rosen
*Assistant Examiner* — Mikail Mannan
(74) *Attorney, Agent, or Firm* — C.R. Bard Intellectual Property Buchalter

(57) ABSTRACT

A catheter system with a proximal end and a distal end element at the proximal end to actuate a device at the distal end of the system, and an actuator element (32) that runs the length of the system, from the actuator element to the device and actuates the device by transmitting a physical force from the proximal end to the distal end and characterized by a pre-tensioner (40) near the distal end of the system, that can be set in a pre-tensioning disposition prior to actuation of the device, the pre-tensioner thereby reducing the magnitude of the physical force that must be transmitted from the proximal end when actuation of the device is required.

7 Claims, 2 Drawing Sheets

(58) Field of Classification Search
CPC ...... A61F 2002/9511; A61F 2002/9517; A61F 2/962; A61F 2002/011; A61F 2/2436
USPC .............................. 623/1.11, 1.12, 1.13, 1.23
See application file for complete search history.

(56) References Cited

U.S. PATENT DOCUMENTS

| | | | |
|---|---|---|---|
| 2,939,680 A | 6/1960 | Powell | |
| 3,070,057 A | 12/1962 | Dezzani | |
| 3,562,427 A | 2/1971 | Yano et al. | |
| 3,585,707 A | 6/1971 | Stevens | |
| 3,871,382 A | 3/1975 | Mann | |
| 3,881,423 A | 5/1975 | Woods et al. | |
| 4,256,113 A | 3/1981 | Chamness | |
| 4,553,545 A | 11/1985 | Maass et al. | |
| 4,580,568 A | 4/1986 | Gianturco | |
| 4,616,648 A | 10/1986 | Simpson | |
| 4,649,922 A | 3/1987 | Wiktor | |
| 4,665,918 A | 5/1987 | Garza et al. | |
| 4,723,547 A | 2/1988 | Kullas et al. | |
| 4,733,665 A | 3/1988 | Palmaz | |
| 4,739,762 A | 4/1988 | Palmaz | |
| 4,748,982 A | 6/1988 | Horzewski et al. | |
| 4,760,622 A | 8/1988 | Rohrman | |
| 4,771,773 A | 9/1988 | Kropf | |
| 4,800,882 A | 1/1989 | Gianturco | |
| 4,856,516 A | 8/1989 | Hillstead | |
| 4,886,062 A | 12/1989 | Wiktor | |
| 4,889,112 A | 12/1989 | Schachner et al. | |
| 4,913,141 A | 4/1990 | Hillstead | |
| 4,913,683 A | 4/1990 | Gregory | |
| 4,921,483 A | 5/1990 | Wijay et al. | |
| 4,969,458 A | 11/1990 | Wiktor | |
| 4,990,151 A | 2/1991 | Wallsten | |
| 5,019,090 A | 5/1991 | Pinchuk | |
| 5,026,377 A | 6/1991 | Burton et al. | |
| 5,045,072 A | 9/1991 | Castillo et al. | |
| 5,049,128 A | 9/1991 | Duquette | |
| 5,054,162 A | 10/1991 | Rogers | |
| 5,102,417 A | 4/1992 | Palmaz | |
| 5,104,404 A | 4/1992 | Wolff | |
| 5,116,365 A | 5/1992 | Hillstead | |
| 5,133,732 A | 7/1992 | Wiktor | |
| 5,135,536 A | 8/1992 | Hillstead | |
| 5,161,547 A | 11/1992 | Tower | |
| 5,163,941 A | 11/1992 | Garth et al. | |
| 5,190,552 A | 3/1993 | Kelman | |
| 5,201,757 A | 4/1993 | Heyn et al. | |
| 5,203,774 A | 4/1993 | Gilson et al. | |
| 5,209,754 A | 5/1993 | Ahluwalia | |
| 5,224,939 A | 7/1993 | Holman et al. | |
| 5,228,452 A | 7/1993 | Samson | |
| 5,242,423 A | 9/1993 | Goodsir et al. | |
| 5,254,107 A | 10/1993 | Soltesz | |
| 5,275,622 A | 1/1994 | Lazarus et al. | |
| 5,279,596 A | 1/1994 | Castaneda et al. | |
| 5,282,824 A | 2/1994 | Gianturco | |
| 5,290,295 A | 3/1994 | Querals et al. | |
| 5,290,310 A | 3/1994 | Makower et al. | |
| 5,292,331 A | 3/1994 | Boneau | |
| 5,312,351 A | 5/1994 | Gerrone | |
| 5,312,363 A | 5/1994 | Ryan et al. | |
| 5,334,147 A | 8/1994 | Johnson | |
| 5,336,192 A | 8/1994 | Palestrant | |
| 5,346,498 A | 9/1994 | Greelis et al. | |
| 5,370,655 A | 12/1994 | Burns | |
| 5,380,283 A | 1/1995 | Johnson | |
| 5,383,892 A | 1/1995 | Cardon et al. | |
| 5,387,235 A | 2/1995 | Chuter | |
| 5,391,172 A | 2/1995 | Williams et al. | |
| 5,399,164 A | 3/1995 | Snoke et al. | |
| 5,405,378 A | 4/1995 | Strecker et al. | |
| 5,411,507 A | 5/1995 | Heckele | |
| 5,415,664 A | 5/1995 | Pinchuk | |
| 5,417,708 A | 5/1995 | Hall et al. | |
| 5,421,955 A | 6/1995 | Lau et al. | |
| 5,433,723 A | 7/1995 | Lindenberg et al. | |
| 5,443,477 A | 8/1995 | Marin et al. | |
| 5,445,646 A | 8/1995 | Euteneuer et al. | |
| 5,449,366 A | 9/1995 | Li | |
| 5,449,373 A | 9/1995 | Pinchasik et al. | |
| 5,456,694 A | 10/1995 | Marin et al. | |
| 5,456,713 A | 10/1995 | Chuter | |
| 5,458,615 A | 10/1995 | Klemm et al. | |
| 5,466,221 A | 11/1995 | Zadini et al. | |
| 5,470,315 A | 11/1995 | Adams | |
| 5,477,856 A | 12/1995 | Lundquist | |
| 5,480,423 A | 1/1996 | Ravenscroft et al. | |
| 5,484,444 A | 1/1996 | Braunschweiler et al. | |
| 5,507,751 A | 4/1996 | Goode et al. | |
| 5,507,768 A | 4/1996 | Lau et al. | |
| 5,507,769 A | 4/1996 | Marin et al. | |
| 5,509,900 A | 4/1996 | Kirkman | |
| 5,514,154 A | 5/1996 | Lau et al. | |
| 5,531,690 A | 7/1996 | Solar | |
| 5,536,248 A | 7/1996 | Weaver et al. | |
| 5,538,510 A | 7/1996 | Fontirroche et al. | |
| 5,542,924 A | 8/1996 | Snoke et al. | |
| 5,556,389 A | 9/1996 | Liprie | |
| 5,562,726 A | 10/1996 | Chuter | |
| 5,562,728 A | 10/1996 | Lazarus et al. | |
| 5,569,296 A | 10/1996 | Marin et al. | |
| 5,571,086 A | 11/1996 | Kaplan et al. | |
| 5,571,172 A | 11/1996 | Chin | |
| 5,573,530 A | 11/1996 | Fleury et al. | |
| 5,578,074 A | 11/1996 | Mirigian | |
| 5,591,172 A | 1/1997 | Bachmann et al. | |
| 5,591,196 A | 1/1997 | Marin et al. | |
| 5,601,568 A | 2/1997 | Chevillon et al. | |
| 5,603,721 A | 2/1997 | Lau et al. | |
| 5,603,801 A | 2/1997 | DeFriese et al. | |
| 5,605,530 A | 2/1997 | Fischell et al. | |
| 5,609,627 A | 3/1997 | Goicoechea et al. | |
| 5,618,300 A | 4/1997 | Marin et al. | |
| 5,628,755 A | 5/1997 | Heller et al. | |
| 5,630,801 A | 5/1997 | Roussigne et al. | |
| 5,645,076 A | 7/1997 | Yoon | |
| 5,649,906 A | 7/1997 | Gory et al. | |
| 5,666,970 A | 9/1997 | Smith | |
| 5,669,936 A | 9/1997 | Lazarus | |
| 5,672,179 A | 9/1997 | Garth et al. | |
| 5,674,208 A | 10/1997 | Berg et al. | |
| 5,674,278 A | 10/1997 | Boneau | |
| 5,681,322 A | 10/1997 | Hartigan, Jr. | |
| 5,683,345 A | 11/1997 | Waksman et al. | |
| 5,683,451 A | 11/1997 | Lenker et al. | |
| 5,690,644 A | 11/1997 | Yurek et al. | |
| 5,693,084 A | 12/1997 | Chuter | |
| 5,695,498 A | 12/1997 | Tower | |
| 5,695,499 A | 12/1997 | Helgerson et al. | |
| 5,695,517 A | 12/1997 | Marin et al. | |
| 5,697,936 A | 12/1997 | Shipko et al. | |
| 5,697,949 A | 12/1997 | Giurtino et al. | |
| 5,704,914 A | 1/1998 | Stocking et al. | |
| 5,707,376 A | 1/1998 | Kavteladze et al. | |
| 5,709,703 A | 1/1998 | Lukic et al. | |
| 5,713,917 A | 2/1998 | Leonhardt et al. | |
| 5,713,948 A | 2/1998 | Uflacker | |
| 5,716,365 A | 2/1998 | Goicoechea et al. | |
| 5,716,393 A | 2/1998 | Lindenberg et al. | |
| 5,720,776 A | 2/1998 | Chuter et al. | |
| 5,725,534 A | 3/1998 | Rasmussen | |
| 5,728,158 A | 3/1998 | Lau et al. | |
| 5,733,267 A | 3/1998 | Del Toro | |
| 5,733,303 A | 3/1998 | Israel et al. | |
| 5,735,893 A | 4/1998 | Lau et al. | |
| 5,738,667 A | 4/1998 | Solar | |
| 5,741,298 A | 4/1998 | MacLeod | |
| 5,743,876 A | 4/1998 | Swanson | |
| 5,749,921 A | 5/1998 | Lenker et al. | |
| 5,755,777 A | 5/1998 | Chuter | |
| 5,759,186 A | 6/1998 | Bachmann et al. | |
| 5,766,184 A | 6/1998 | Matsuno et al. | |
| 5,769,871 A | 6/1998 | Mers Kelly et al. | |

(56) References Cited

U.S. PATENT DOCUMENTS

| | | |
|---|---|---|
| 5,776,141 A | 7/1998 | Klein et al. |
| 5,776,142 A | 7/1998 | Gunderson |
| 5,776,161 A | 7/1998 | Globerman et al. |
| 5,776,186 A | 7/1998 | Uflacker |
| 5,780,807 A | 7/1998 | Saunders |
| 5,782,855 A | 7/1998 | Lau et al. |
| 5,788,707 A | 8/1998 | Del Toro et al. |
| 5,795,325 A | 8/1998 | Valley et al. |
| 5,800,456 A | 9/1998 | Maeda et al. |
| 5,800,520 A | 9/1998 | Fogarty et al. |
| 5,807,241 A | 9/1998 | Heimberger et al. |
| 5,807,327 A | 9/1998 | Green et al. |
| 5,810,768 A | 9/1998 | Lopez |
| 5,810,837 A | 9/1998 | Hofmann et al. |
| 5,810,869 A | 9/1998 | Kaplan et al. |
| 5,810,872 A | 9/1998 | Kanesaka et al. |
| 5,814,062 A | 9/1998 | Sepetka et al. |
| 5,824,058 A | 10/1998 | Ravenscroft et al. |
| 5,833,694 A | 11/1998 | Poncet |
| 5,840,064 A | 11/1998 | Liprie |
| 5,843,088 A | 12/1998 | Barra et al. |
| 5,843,092 A | 12/1998 | Heller et al. |
| 5,843,120 A | 12/1998 | Israel et al. |
| 5,843,244 A | 12/1998 | Pelton et al. |
| 5,851,210 A | 12/1998 | Torossian |
| 5,860,998 A | 1/1999 | Robinson et al. |
| RE36,104 E | 2/1999 | Solar |
| 5,868,755 A | 2/1999 | Kanner et al. |
| 5,873,906 A | 2/1999 | Lau et al. |
| 5,879,382 A | 3/1999 | Boneau |
| 5,891,154 A | 4/1999 | Loeffler |
| 5,904,648 A | 5/1999 | Arndt et al. |
| 5,906,579 A | 5/1999 | Vander Salm et al. |
| 5,906,619 A | 5/1999 | Olson et al. |
| 5,910,145 A | 6/1999 | Fischell et al. |
| 5,913,897 A | 6/1999 | Corso, Jr. et al. |
| 5,919,225 A | 7/1999 | Lau et al. |
| 5,925,061 A | 7/1999 | Ogi et al. |
| 5,928,246 A | 7/1999 | Gordon et al. |
| 5,931,842 A | 8/1999 | Goldsteen et al. |
| 5,944,727 A | 8/1999 | Ahari et al. |
| 5,951,585 A | 9/1999 | Cathcart et al. |
| 5,954,729 A | 9/1999 | Bachmann et al. |
| 5,961,536 A | 10/1999 | Mickley et al. |
| 5,968,052 A | 10/1999 | Sullivan, III et al. |
| 5,968,053 A | 10/1999 | Revelas |
| 5,968,061 A | 10/1999 | Mirza |
| 5,968,068 A | 10/1999 | Dehdashtian et al. |
| 5,968,069 A | 10/1999 | Dusbabek et al. |
| 5,972,018 A | 10/1999 | Israel et al. |
| 5,980,515 A | 11/1999 | Tu |
| 5,984,225 A | 11/1999 | Enzinna |
| 5,992,000 A | 11/1999 | Humphrey et al. |
| 5,997,562 A | 12/1999 | Zadno-Azizi et al. |
| 6,004,328 A | 12/1999 | Solar |
| 6,015,429 A | 1/2000 | Lau et al. |
| 6,019,778 A | 2/2000 | Wilson et al. |
| 6,027,509 A | 2/2000 | Schatz et al. |
| 6,039,744 A | 3/2000 | Forber |
| 6,039,749 A | 3/2000 | Marin et al. |
| 6,042,597 A | 3/2000 | Kveen et al. |
| 6,045,536 A | 4/2000 | Meier et al. |
| 6,071,263 A | 6/2000 | Kirkman |
| 6,071,286 A | 6/2000 | Mawad |
| 6,077,295 A | 6/2000 | Limon et al. |
| 6,080,140 A | 6/2000 | Swaminathan et al. |
| 6,083,194 A | 7/2000 | Lopez |
| 6,090,035 A | 7/2000 | Campbell et al. |
| 6,090,063 A | 7/2000 | Makower et al. |
| 6,090,128 A | 7/2000 | Douglas |
| 6,096,009 A | 8/2000 | Windheuser et al. |
| 6,096,045 A | 8/2000 | Del Toro et al. |
| 6,096,056 A | 8/2000 | Brown |
| 6,102,890 A | 8/2000 | Stivland et al. |
| 6,102,942 A | 8/2000 | Ahari |
| 6,110,191 A | 8/2000 | Dehdashtian et al. |
| 6,113,607 A | 9/2000 | Lau et al. |
| 6,117,140 A | 9/2000 | Munsinger |
| 6,117,165 A | 9/2000 | Becker |
| 6,117,167 A | 9/2000 | Goicoechea et al. |
| 6,123,723 A | 9/2000 | Konya et al. |
| 6,129,755 A | 10/2000 | Mathis et al. |
| 6,136,007 A | 10/2000 | Goldsteen et al. |
| 6,136,572 A | 10/2000 | Benatti et al. |
| 6,143,014 A | 11/2000 | Dehdashtian et al. |
| 6,143,021 A | 11/2000 | Staehle |
| 6,146,415 A | 11/2000 | Fitz |
| 6,149,680 A | 11/2000 | Shelso et al. |
| 6,156,053 A | 12/2000 | Gandhi et al. |
| 6,156,054 A | 12/2000 | Zadno-Azizi et al. |
| 6,156,063 A | 12/2000 | Douglas |
| 6,159,228 A | 12/2000 | Frid et al. |
| 6,159,239 A | 12/2000 | Greenhalgh |
| 6,167,315 A | 12/2000 | Coe et al. |
| 6,168,610 B1 | 1/2001 | Marin et al. |
| 6,168,617 B1 | 1/2001 | Blaeser et al. |
| 6,174,327 B1 | 1/2001 | Mertens et al. |
| 6,183,509 B1 | 2/2001 | Dibie |
| 6,190,360 B1 | 2/2001 | Iancea et al. |
| 6,190,393 B1 | 2/2001 | Bevier et al. |
| 6,190,406 B1 | 2/2001 | Duerig et al. |
| 6,203,550 B1 | 3/2001 | Olson |
| 6,203,558 B1 | 3/2001 | Dusbabek et al. |
| 6,210,422 B1 | 4/2001 | Douglas |
| 6,214,026 B1 | 4/2001 | Lepak et al. |
| 6,217,585 B1 | 4/2001 | Houser et al. |
| 6,224,608 B1 | 5/2001 | Ciccolella et al. |
| 6,238,402 B1 | 5/2001 | Sullivan, III et al. |
| 6,238,415 B1 | 5/2001 | Sepetka et al. |
| 6,238,837 B1 | 5/2001 | Fan |
| 6,241,692 B1 | 6/2001 | Tu et al. |
| 6,245,100 B1 | 6/2001 | Davila et al. |
| 6,248,122 B1 | 6/2001 | Klumb et al. |
| 6,251,132 B1 | 6/2001 | Ravenscroft et al. |
| 6,254,608 B1 | 7/2001 | Solar |
| 6,264,689 B1 | 7/2001 | Colgan et al. |
| 6,270,521 B1 | 8/2001 | Fischell et al. |
| 6,273,879 B1 | 8/2001 | Keith et al. |
| 6,273,895 B1 | 8/2001 | Pinchuk et al. |
| 6,287,322 B1 | 9/2001 | Zhu et al. |
| 6,312,407 B1 | 11/2001 | Zadno-Azizi et al. |
| 6,319,262 B1 | 11/2001 | Bates et al. |
| 6,332,403 B1 | 12/2001 | Weise et al. |
| 6,342,067 B1 | 1/2002 | Mathis et al. |
| 6,344,053 B1 | 2/2002 | Boneau |
| 6,346,118 B1 | 2/2002 | Baker et al. |
| 6,348,065 B1 | 2/2002 | Brown et al. |
| 6,358,274 B1 | 3/2002 | Thompson |
| 6,368,344 B1 | 4/2002 | Fitz |
| 6,375,676 B1 | 4/2002 | Cox |
| 6,383,211 B1 | 5/2002 | Staehle |
| 6,391,050 B1 | 5/2002 | Broome |
| 6,391,051 B2 | 5/2002 | Sullivan, III et al. |
| 6,395,020 B1 | 5/2002 | Ley et al. |
| 6,402,760 B1 | 6/2002 | Fedida |
| 6,413,269 B1 | 7/2002 | Bui et al. |
| 6,425,898 B1 | 7/2002 | Wilson et al. |
| 6,443,979 B1 | 9/2002 | Stalker et al. |
| 6,443,982 B1 | 9/2002 | Israel et al. |
| 6,461,381 B2 | 10/2002 | Israel et al. |
| 6,471,673 B1 | 10/2002 | Kastenhofer |
| 6,488,703 B1 | 12/2002 | Kveen et al. |
| 6,500,248 B1 | 12/2002 | Hayashi |
| 6,514,261 B1 | 2/2003 | Randall et al. |
| 6,517,569 B2 | 2/2003 | Mikus et al. |
| 6,520,938 B1 | 2/2003 | Funderburk et al. |
| 6,520,983 B1 | 2/2003 | Colgan et al. |
| 6,527,779 B1 | 3/2003 | Rourke |
| 6,527,789 B1 | 3/2003 | Lau et al. |
| 6,544,278 B1 * | 4/2003 | Vrba et al. .................. 606/198 |
| 6,569,181 B1 | 5/2003 | Burns |
| 6,572,643 B1 | 6/2003 | Gharibadeh |
| 6,575,993 B1 | 6/2003 | Yock |
| 6,582,459 B1 | 6/2003 | Lau et al. |

(56) References Cited

U.S. PATENT DOCUMENTS

| | | |
|---|---|---|
| 6,582,460 B1 | 6/2003 | Cryer |
| 6,599,296 B1 | 7/2003 | Gillick et al. |
| 6,613,014 B1 | 9/2003 | Chi |
| 6,613,075 B1 | 9/2003 | Healy et al. |
| 6,629,981 B2 | 10/2003 | Bui et al. |
| 6,645,238 B2 | 11/2003 | Smith |
| 6,652,506 B2 | 11/2003 | Bowe et al. |
| 6,659,977 B2 | 12/2003 | Kastenhofer |
| 6,660,031 B2 | 12/2003 | Tran et al. |
| 6,660,827 B2 | 12/2003 | Loomis et al. |
| 6,663,666 B1 | 12/2003 | Quiachon et al. |
| 6,695,862 B2 | 2/2004 | Cox et al. |
| 6,716,190 B1 | 4/2004 | Glines et al. |
| 6,716,238 B2 | 4/2004 | Elliott |
| 6,749,627 B2 | 6/2004 | Thompson et al. |
| 6,755,854 B2 | 6/2004 | Gillick et al. |
| 6,773,446 B1 | 8/2004 | Dwyer et al. |
| 6,786,918 B1 | 9/2004 | Krivoruchko et al. |
| 6,821,292 B2 | 11/2004 | Pazienza et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,913,613 B2 | 7/2005 | Schwarz et al. |
| 6,939,352 B2 | 9/2005 | Buzzard et al. |
| 6,939,370 B2 | 9/2005 | Hartley et al. |
| 7,033,368 B2 | 4/2006 | Rourke |
| 7,052,511 B2 | 5/2006 | Weldon et al. |
| 7,122,050 B2 | 10/2006 | Randall et al. |
| 7,172,617 B2 | 2/2007 | Colgan et al. |
| 7,294,135 B2 | 11/2007 | Stephens et al. |
| 7,323,006 B2 | 1/2008 | Andreas et al. |
| 7,381,216 B2 | 6/2008 | Buzzard et al. |
| D576,725 S | 9/2008 | Shumer et al. |
| D578,216 S | 10/2008 | Dorn et al. |
| D578,643 S | 10/2008 | Shumer et al. |
| D578,644 S | 10/2008 | Shumer et al. |
| D578,645 S | 10/2008 | Shumer et al. |
| 7,506,650 B2 | 3/2009 | Lowe et al. |
| 7,550,001 B2 | 6/2009 | Dorn et al. |
| 7,553,322 B2 | 6/2009 | Dorn et al. |
| 7,556,641 B2 * | 7/2009 | Cully et al. .................. 623/1.11 |
| D598,543 S | 8/2009 | Vogel et al. |
| 7,582,054 B2 | 9/2009 | Okada |
| 7,935,141 B2 | 5/2011 | Randall et al. |
| 8,062,344 B2 | 11/2011 | Dorn et al. |
| 8,075,606 B2 | 12/2011 | Dorn |
| 8,382,813 B2 | 2/2013 | Shumer |
| 8,419,784 B2 | 4/2013 | Matsuoka et al. |
| 8,500,789 B2 | 8/2013 | Wuebbeling et al. |
| 2001/0007082 A1 | 7/2001 | Dusbabek et al. |
| 2001/0044621 A1 | 11/2001 | Klumb et al. |
| 2001/0051822 A1 | 12/2001 | Stack et al. |
| 2002/0004663 A1 | 1/2002 | Gittings et al. |
| 2002/0035394 A1 | 3/2002 | Fierens et al. |
| 2002/0045929 A1 | 4/2002 | Diaz |
| 2002/0052642 A1 | 5/2002 | Cox et al. |
| 2002/0116044 A1 | 8/2002 | Cottone et al. |
| 2002/0128678 A1 * | 9/2002 | Petersen ............... A61F 2/013 |
| | | 606/200 |
| 2002/0151955 A1 | 10/2002 | Tran et al. |
| 2002/0183827 A1 | 12/2002 | Derus et al. |
| 2002/0188341 A1 | 12/2002 | Elliott |
| 2003/0028236 A1 | 2/2003 | Gillick et al. |
| 2003/0049295 A1 | 3/2003 | Guggenbichler et al. |
| 2003/0050686 A1 | 3/2003 | Raeder-Devens et al. |
| 2003/0074043 A1 | 4/2003 | Thompson |
| 2003/0074045 A1 | 4/2003 | Buzzard et al. |
| 2003/0105451 A1 | 6/2003 | Westlund et al. |
| 2003/0135162 A1 | 7/2003 | Deyette et al. |
| 2003/0163085 A1 | 8/2003 | Tanner et al. |
| 2003/0167060 A1 | 9/2003 | Buzzard et al. |
| 2003/0191516 A1 | 10/2003 | Weldon et al. |
| 2003/0208262 A1 | 11/2003 | Gaber |
| 2004/0006380 A1 | 1/2004 | Buck et al. |
| 2004/0098079 A1 | 5/2004 | Hartley et al. |
| 2004/0098083 A1 | 5/2004 | Tran et al. |
| 2004/0143160 A1 | 7/2004 | Couvillon |
| 2004/0148009 A1 | 7/2004 | Buzzard et al. |
| 2004/0153137 A1 | 8/2004 | Gaschino et al. |
| 2004/0186547 A1 | 9/2004 | Dorn et al. |
| 2004/0193180 A1 | 9/2004 | Buzzard et al. |
| 2004/0193283 A1 | 9/2004 | Rioux et al. |
| 2005/0004515 A1 | 1/2005 | Hart et al. |
| 2005/0021123 A1 | 1/2005 | Dorn et al. |
| 2005/0027306 A1 | 2/2005 | Krivoruchko et al. |
| 2005/0027345 A1 | 2/2005 | Horan et al. |
| 2005/0033402 A1 | 2/2005 | Cully et al. |
| 2005/0043618 A1 | 2/2005 | Mansouri-Ruiz |
| 2005/0043713 A1 | 2/2005 | Zhou |
| 2005/0060016 A1 | 3/2005 | Wu et al. |
| 2005/0080476 A1 | 4/2005 | Gunderson et al. |
| 2005/0085851 A1 | 4/2005 | Fiehler et al. |
| 2005/0090887 A1 | 4/2005 | Pryor |
| 2005/0090890 A1 | 4/2005 | Wu et al. |
| 2005/0149159 A1 | 7/2005 | Andreas et al. |
| 2005/0159725 A1 | 7/2005 | Tockman et al. |
| 2005/0182475 A1 | 8/2005 | Jen et al. |
| 2005/0209670 A1 | 9/2005 | George et al. |
| 2005/0209672 A1 | 9/2005 | George et al. |
| 2005/0209674 A1 | 9/2005 | Kutscher et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288764 A1 | 12/2005 | Snow et al. |
| 2006/0058866 A1 | 3/2006 | Cully et al. |
| 2006/0074477 A1 | 4/2006 | Berthiaume et al. |
| 2006/0085057 A1 | 4/2006 | George et al. |
| 2006/0095116 A1 | 5/2006 | Bolduc et al. |
| 2006/0100686 A1 | 5/2006 | Bolduc et al. |
| 2006/0167467 A1 | 7/2006 | Rourke |
| 2006/0173525 A1 * | 8/2006 | Behl ..................... A61F 2/95 |
| | | 623/1.11 |
| 2006/0241737 A1 | 10/2006 | Tockman et al. |
| 2006/0259124 A1 | 11/2006 | Matsuoka et al. |
| 2006/0276873 A1 | 12/2006 | Sato |
| 2007/0016164 A1 | 1/2007 | Dudney et al. |
| 2007/0050006 A1 | 3/2007 | Lavelle |
| 2007/0055339 A1 | 3/2007 | George et al. |
| 2007/0055342 A1 | 3/2007 | Wu et al. |
| 2007/0060999 A1 | 3/2007 | Randall et al. |
| 2007/0073379 A1 | 3/2007 | Chang |
| 2007/0073389 A1 | 3/2007 | Bolduc et al. |
| 2007/0088421 A1 | 4/2007 | Loewen |
| 2007/0100420 A1 | 5/2007 | Kavanagh et al. |
| 2007/0100422 A1 | 5/2007 | Shumer et al. |
| 2007/0100429 A1 | 5/2007 | Wu et al. |
| 2007/0112409 A1 | 5/2007 | Wu et al. |
| 2007/0118201 A1 | 5/2007 | Pappas et al. |
| 2007/0118206 A1 | 5/2007 | Colgan et al. |
| 2007/0156222 A1 | 7/2007 | Feller et al. |
| 2007/0156224 A1 | 7/2007 | Cioanta et al. |
| 2007/0168014 A1 | 7/2007 | Jimenez et al. |
| 2007/0191864 A1 | 8/2007 | Shumer |
| 2007/0191865 A1 | 8/2007 | Pappas |
| 2007/0191925 A1 | 8/2007 | Dorn |
| 2007/0194483 A1 | 8/2007 | Guggenbichler et al. |
| 2007/0233222 A1 | 10/2007 | Roeder et al. |
| 2007/0244540 A1 | 10/2007 | Pryor |
| 2007/0255390 A1 | 11/2007 | Ducke et al. |
| 2009/0024133 A1 | 1/2009 | Keady et al. |
| 2009/0099638 A1 | 4/2009 | Grewe |
| 2010/0004606 A1 | 1/2010 | Hansen et al. |
| 2010/0036472 A1 | 2/2010 | Papp |
| 2010/0094399 A1 | 4/2010 | Dorn et al. |
| 2010/0161024 A1 * | 6/2010 | Kennedy, II et al. ....... 623/1.11 |
| 2010/0168756 A1 | 7/2010 | Dorn et al. |
| 2010/0174290 A1 | 7/2010 | Wuebbeling et al. |
| 2013/0317592 A1 | 11/2013 | Wubbeling et al. |

FOREIGN PATENT DOCUMENTS

| | | |
|---|---|---|
| DE | 02544371 A1 | 4/1976 |
| DE | 03132323 A1 | 4/1983 |
| DE | 3219629 A1 | 12/1983 |

(56) References Cited

FOREIGN PATENT DOCUMENTS

| | | |
|---|---|---|
| DE | 4133696 A1 | 4/1993 |
| DE | 04420142 A1 | 12/1995 |
| DE | 29516712 U1 | 12/1995 |
| DE | 19539449 A1 | 4/1997 |
| DE | 29717110 U1 | 11/1997 |
| DE | 29816878 U1 | 12/1998 |
| DE | 29522101 | 12/1999 |
| DE | 19921530 | 6/2000 |
| DE | 19901530 A1 | 7/2000 |
| DE | 19936059 A1 | 2/2001 |
| DE | 20000659 U1 | 5/2001 |
| DE | 69521346 T2 | 4/2002 |
| EP | 0436303 A1 | 7/1991 |
| EP | 0505686 A1 | 9/1992 |
| EP | 0518838 A1 | 12/1992 |
| EP | 0564894 A1 | 10/1993 |
| EP | 0611556 A1 | 8/1994 |
| EP | 0630657 A1 | 12/1994 |
| EP | 0633756 B1 | 1/1995 |
| EP | 0688545 A1 | 12/1995 |
| EP | 0699451 A2 | 3/1996 |
| EP | 0712614 A1 | 5/1996 |
| EP | 0744930 A1 | 12/1996 |
| EP | 0747021 A2 | 12/1996 |
| EP | 0752896 B1 | 1/1997 |
| EP | 0790041 A2 | 8/1997 |
| EP | 0792627 A2 | 9/1997 |
| EP | 0873733 A1 | 10/1998 |
| EP | 0876804 A1 | 11/1998 |
| EP | 0947212 A2 | 10/1999 |
| EP | 1025813 A2 | 8/2000 |
| EP | 1078611 A1 | 2/2001 |
| EP | 1095634 A2 | 5/2001 |
| EP | 1117341 A1 | 7/2001 |
| EP | 1132058 A1 | 9/2001 |
| EP | 1155664 A2 | 11/2001 |
| EP | 1181906 A2 | 2/2002 |
| EP | 1199051 A2 | 4/2002 |
| EP | 1290989 A2 | 3/2003 |
| EP | 1299050 B1 | 4/2003 |
| EP | 1302178 A2 | 4/2003 |
| EP | 1383446 A1 | 1/2004 |
| EP | 1440671 A2 | 7/2004 |
| EP | 1447057 A1 | 8/2004 |
| EP | 1447058 A1 | 8/2004 |
| EP | 1637092 A2 | 3/2006 |
| FR | 2760351 A1 | 9/1998 |
| FR | 2797761 A1 | 3/2001 |
| JP | 2003518406 A | 6/2003 |
| JP | 2004147812 A | 5/2004 |
| JP | 2005530558 A | 10/2005 |
| JP | 2005532100 A | 10/2005 |
| JP | 2007-097620 A | 4/2007 |
| JP | 2007-508045 A | 4/2007 |
| MX | 303207 | 12/2012 |
| WO | 9521593 A1 | 8/1995 |
| WO | 9526775 A1 | 10/1995 |
| WO | 9618359 A1 | 6/1996 |
| WO | 9618361 A1 | 6/1996 |
| WO | 9809584 A1 | 3/1998 |
| WO | 9820811 A1 | 5/1998 |
| WO | 9823241 A2 | 6/1998 |
| WO | 9830173 A1 | 7/1998 |
| WO | WO9827894 * 7/1998 ............... A61F 2/06 |
| WO | 9852496 A1 | 11/1998 |
| WO | 9904728 A1 | 2/1999 |
| WO | 9925280 A1 | 5/1999 |
| WO | 9944541 A1 | 9/1999 |
| WO | 9947075 A1 | 9/1999 |
| WO | 9951167 A2 | 10/1999 |
| WO | 0000104 A1 | 1/2000 |
| WO | 0002503 A1 | 1/2000 |
| WO | 0016718 A1 | 3/2000 |
| WO | 0018330 A1 | 4/2000 |
| WO | 0067675 A1 | 11/2000 |
| WO | 0069368 A2 | 11/2000 |
| WO | 0071059 A1 | 11/2000 |
| WO | 0078246 A2 | 12/2000 |
| WO | 0078248 A1 | 12/2000 |
| WO | 0132102 A1 | 5/2001 |
| WO | 0134061 A1 | 5/2001 |
| WO | 0147436 A2 | 7/2001 |
| WO | 0158387 A1 | 8/2001 |
| WO | 0189421 | 11/2001 |
| WO | 0203888 A2 | 1/2002 |
| WO | 0203889 A2 | 1/2002 |
| WO | 02066094 A2 | 8/2002 |
| WO | 02083036 A2 | 10/2002 |
| WO | 02087470 A1 | 11/2002 |
| WO | 02102279 A2 | 12/2002 |
| WO | 03002020 A2 | 1/2003 |
| WO | 03003926 A1 | 1/2003 |
| WO | 03061724 A2 | 7/2003 |
| WO | 2004004597 A2 | 1/2004 |
| WO | 2004066809 A2 | 8/2004 |
| WO | 2005039448 A1 | 5/2005 |
| WO | 2005053574 A2 | 6/2005 |
| WO | 2005062980 A2 | 7/2005 |
| WO | 2005065200 A2 | 7/2005 |
| WO | 2005117759 A2 | 12/2005 |
| WO | 2006071915 A2 | 7/2006 |
| WO | 2006104143 A1 | 10/2006 |
| WO | 2007002713 A2 | 1/2007 |
| WO | 2007005799 A1 | 1/2007 |
| WO | 2007022395 A1 | 2/2007 |
| WO | 2007029242 A1 | 3/2007 |
| WO | 2007044929 A1 | 4/2007 |
| WO | 2007083470 A1 | 7/2007 |
| WO | 2008034793 A1 | 3/2008 |
| WO | 2010027998 A1 | 3/2010 |

OTHER PUBLICATIONS

U.S. Appl. No. 11/652,737, filed Jan. 12, 2007 Non-Final Office Action dated Apr. 12, 2013.
U.S. Appl. No. 11/652,737, filed Jan. 12, 2007 Non-Final Office Action dated Feb. 12, 2014.
U.S. Appl. No. 11/652,737, filed Jan. 12, 2007 Advisory Action dated Dec. 30, 2013.
U.S. Appl. No. 11/652,737, filed Jan. 12, 2007 Final Office Action dated Oct. 22, 2013.
U.S. Appl. No. 11/652,737, filed Jan. 12, 2007 Notice of Allowance dated Apr. 25, 2014.
U.S. Appl. No. 12/376,670, filed Feb. 6, 2009 Final Office Action dated Dec. 17, 2013.
U.S. Appl. No. 12/376,670, filed Feb. 6, 2009 Non-Final Office Action dated Jun. 21, 2012.
U.S. Appl. No. 12/640,956, filed Dec. 17, 2009 Non-Final Office Action dated Jan. 24, 2011.
U.S. Appl. No. 12/640,956, filed Dec. 17, 2009 Notice of Allowancwe dated Jul. 13, 2011.
U.S. Appl. No. 12/668,613, filed Feb. 19, 2010 Non-Final Office Action dated Nov. 26, 2012.
"Medtronic Announces FDA Clearance of Bridge SE Biliary Stent." Business Wire, Oct. 15, 2001. www.medtronic.com/newsroom/news_20011015a.html.
"Summary for the Bridge SE Biliary Self-Expanding Stent Delivery System" Jan. 14, 2002 FDA Section 510 (k) review.
Bridge™ Se Binary Stent System, <<http:/www.medtronicave/com/includes/content/phsycians/bridges/htm>>, 3 last pages, last accessed Oct. 2002.
EP 10001359.8 filed Aug. 16, 2006 European Search Report dated May 28, 2010.
EP 13170019.7 extended European Search Report dated Aug. 5, 2013.
EP 14151266.5 extended European Search Report dated Apr. 9, 2014.
JP 2008-550429 filed Jun. 27, 2008 Final Notice of Reason for Rejection dated Oct. 25, 2012.
JP 2008-550429 filed Jun. 27, 2008 Office Action dated Jan. 4, 2012.

(56) References Cited

OTHER PUBLICATIONS

JP 2010-515514 Notice of Reason for Rejection dated Dec. 20, 2012.
JP 2013-011060 first Official Action dated Feb. 21, 2014.
JP 2013-089100 Official Action dated Apr. 8, 2014.
PCT/EP2002/004727 filed Apr. 29, 2002 Preliminary Examination Report dated Jan. 7, 2003.
PCT/EP2002/004727 filed Apr. 29, 2002 Search Report dated Jul. 10, 2002.
PCT/EP2002/006784 filed Jun. 19, 2002 Preliminary Examination Report dated Apr. 14, 2004.
PCT/EP2002/006784 filed Jun. 19, 2002 Search Report dated Jan. 21, 2004.
PCT/EP2007/058205 filed Aug. 7, 2007 Preliminary Report on Patentability dated Aug. 4, 2008.
PCT/EP2007/058205 filed Aug. 7, 2007 Search Report dated Nov. 30, 2007.
PCT/EP2007/058205 filed Aug. 7, 2007 Written Opinion Nov. 30, 2007.
PCT/EP2008/059040 filed Jul. 1, 2008 Search Report dated Nov. 4, 2008.
PCT/EP2008/059040 filed Jul. 10, 2008 Preliminary Report on Patentability dated Sep. 29, 2009.
PCT/EP2008/059040 filed Jul. 10, 2008 Written Opinion dated Nov. 4, 2008.
PCT/EP2011/068238 filed Oct. 19, 2011 International Preliminary Report on Patentability dated Apr. 23, 2013.
PCT/US2005/019860 filed Jun. 6, 2005 Preliminary Report on Patentability dated Dec. 4, 2006.
PCT/US2005/019860 filed Jun. 6, 2005 Search Report dated Dec. 15, 2005.
PCT/US2005/019860 filed Jun. 6, 2005 Written Opinion dated Dec. 15, 2005.
PCT/US2006/032228 filed Aug. 16, 2006 Preliminary Report on Patentability dated Feb. 20, 2008.
PCT/US2006/032228 filed Aug. 16, 2008 Search Report dated Jan. 19, 2007.
PCT/US2006/032228 filed Aug. 16, 2006 Written Opinion dated Jan. 19, 2007.
PCT/US2007/000834 filed Jan. 12, 2007 Preliminary Report on Patentability Jul. 15, 2008.
PCT/US2007/000834 filed Jan. 12, 2007 Search Report dated Apr. 27, 2007.
PCT/US2007/000834 filed Jan. 12, 2007 Written Opinion dated Apr. 27, 2007.
U.S. Appl. No. 10/476,351, filed May 7, 2004 Final Office Action dated Feb. 4, 2009.
U.S. Appl. No. 10/476,351, filed May 7, 2004 Final Office Action dated Oct. 21, 2008.
U.S. Appl. No. 10/476,351, filed May 7, 2004 Non-Final Office Action dated Apr. 4, 2008.
U.S. Appl. No. 10/476,351, filed May 7, 2004 Notice of Allowance dated Mar. 12, 2009.
U.S. Appl. No. 10/824,033, filed Apr. 14, 2004 Non-Final Office Action dated Jul. 17, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Aug. 31, 2009.
U.S. Appl. No. 11/505,185, filed Aug. 16, 2006 Non-Final Office Action dated Oct. 7, 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated May 27, 2009.
U.S. Appl. No. 11/652,737, filed Jan. 12, 2007 Final Office Action dated Jun. 10, 2010.
U.S. Appl. No. 11/652,737, filed Jan. 12, 2007 Non-Final Office Action dated Oct. 27, 2009.

* cited by examiner

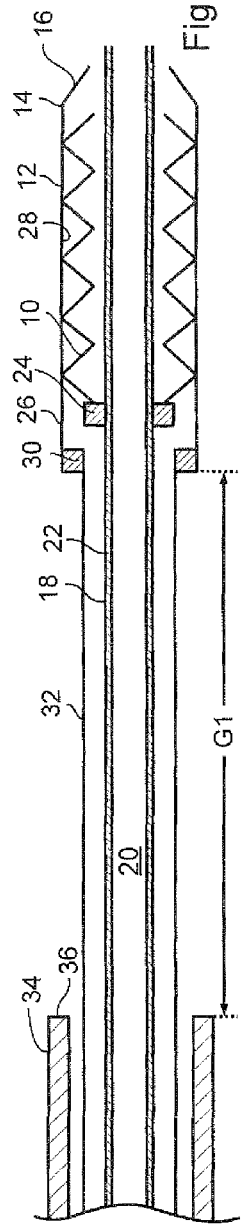
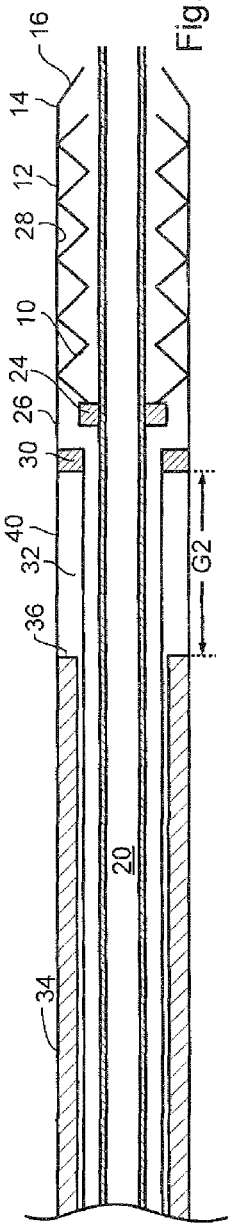
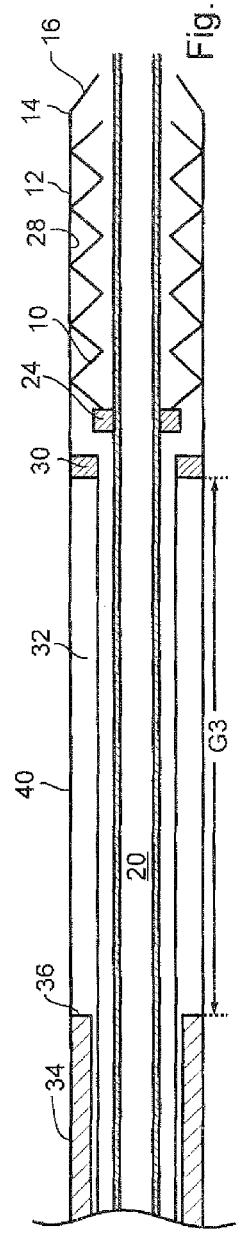
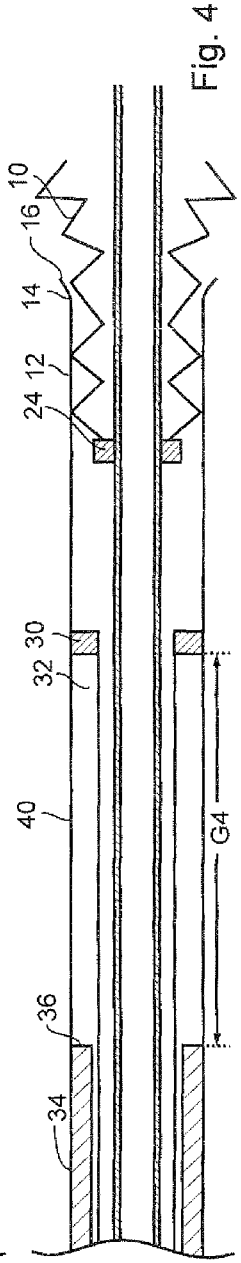

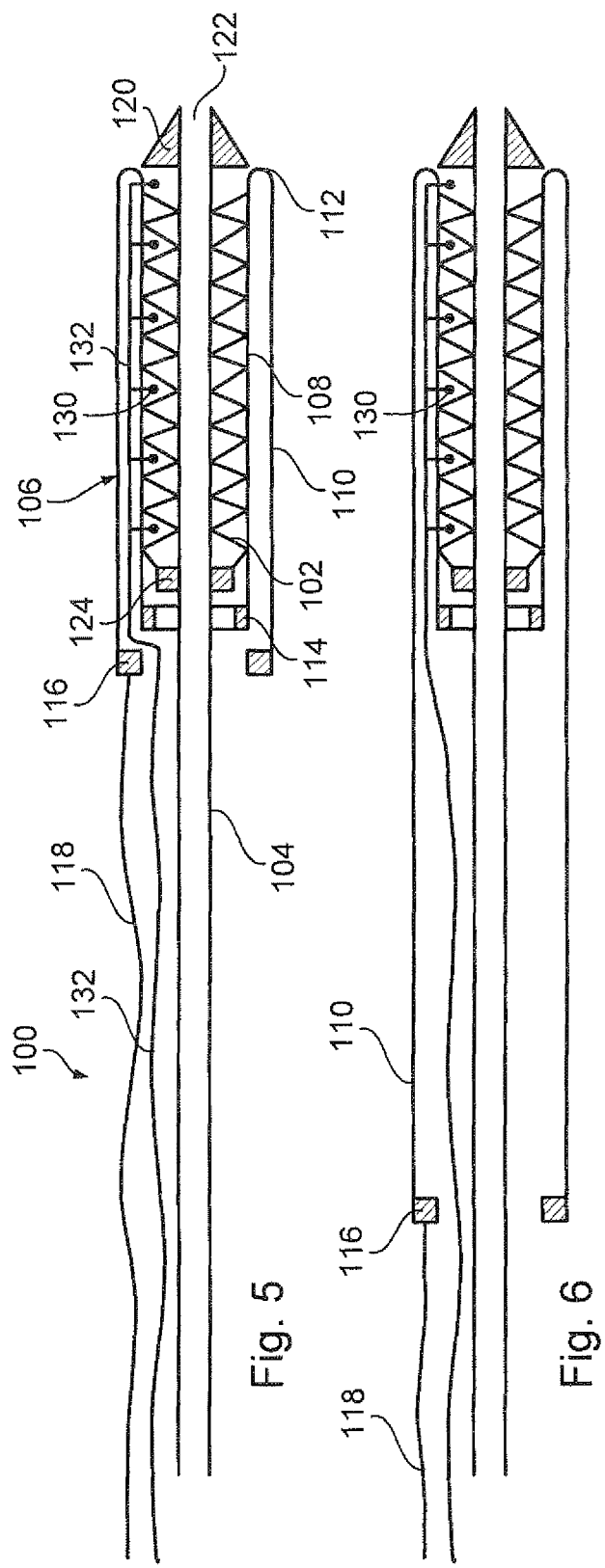
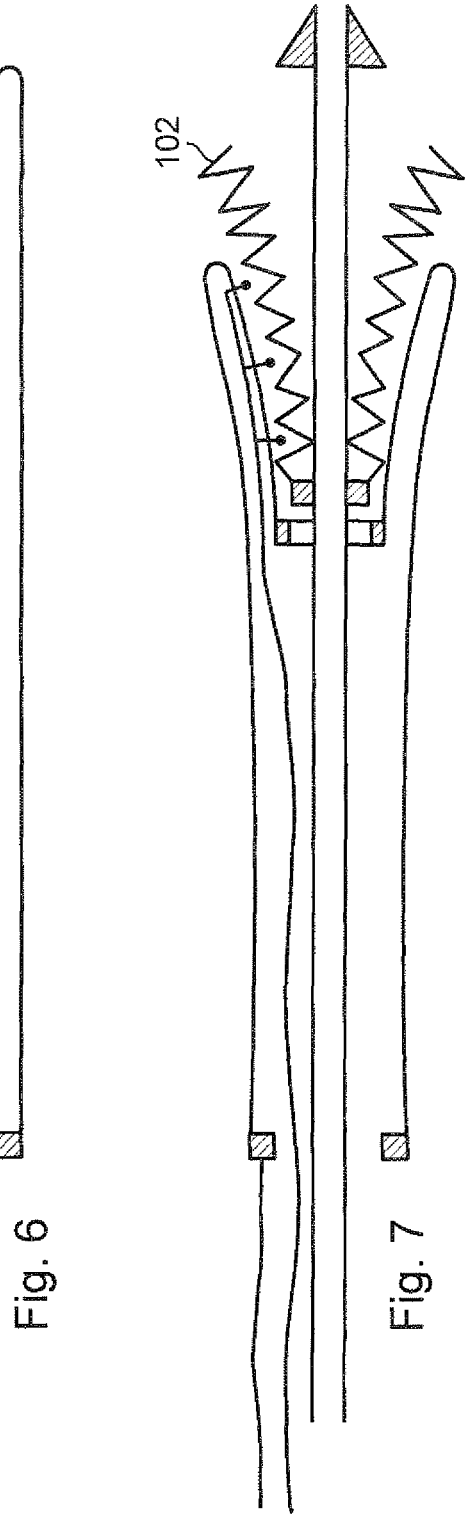

SYSTEM TO DELIVER A BODILY IMPLANT

PRIORITY

This application is a U.S. national stage application under 35 U.S.C. §371 of International Application No. PCT/EP2011/068238, filed Oct. 19, 2011, claiming priority to United Kingdom Patent Application No. 1017834.1, filed Oct. 21, 2010, and to U.S. Provisional Application No. 61/405,514, filed Oct. 21, 2010, each of which is incorporated by reference in its entirety into this application.

TECHNICAL FIELD

This invention relates to a transluminal catheter-type system to deliver a bodily implant such as a self-expanding stent, the system having a proximal end with an implant release means and a distal end that carries the implant radially confined within a sheath which, to release the implant, is pulled proximally from the proximal end of the system by the release means to translate the sheath proximally relative to the implant to release the implant from its radial confinement, progressively, starting at the distal end of the implant. The delivery may be via a vascular lumen but could be via a bodily lumen not part of the vascular system. The implant need not be a stent but could be something else, such as a valve or a filter for placement in the bodily lumen.

TECHNICAL BACKGROUND

The archetypal catheter-type system to release a self-expanding stent into a bodily lumen takes the form of a catheter shaft extending between a proximal end of the system that remains outside the body and a distal end of the system that carries the stent. The proximal end is manipulated, to release the stent. This manipulation involves pulling on one component of the system, at the proximal end, in order to pull back proximally a sheath that radially confines the stent.

Since the stent is exerting radially outward force on the sheath, up to the time that the stent is released from the sheath, the stent will tend to be carried with the sheath, whenever the sheath is pulled proximally, relative to the shaft of the catheter system. Thus, that shaft needs to engage with a surface portion of the stent and restrain the stent as the sheath retracts proximally, relative to the stent. This restraining of the stent naturally imposes on the catheter shaft an endwise compressive stress, as that shaft "pushes" on the stent during proximal withdrawal of the sheath.

Thus, the shaft of the catheter system inherently includes components that are sliding over each other, throughout the length of the system, which length can be rather large, typically between 100 cm and 150 cm.

As experience grows, self-expanding stents can be delivered to ever more demanding locations in the body, with the delivery system advancing along ever more tortuous and confined lumens. Today, there is vigorous demand for delivery systems that can keep to an overall diameter of 6 F or smaller (6 F equals 2 mm, with the unit of "1 French" corresponding to ⅓ mm). As the diameter is continually brought down, so the pressure on the system designer increases, to minimise the forces of friction that arise with sliding contact along the shaft length.

Further, with greater radial force, greater axial length, and with ever more sophisticated coverings on the stent strut matrix the "drag" of the stent on the proximally-moving sheath gets bigger. This, in turn, raises the tension required in the stent release means. It can well be imagined that a need therefore exists to hold down the absolute values of endwise tensile stress, to values that the system can tolerate without kinking or buckling and without failure of any one of the very long, very thin components involved.

SUMMARY OF THE INVENTION

The invention is defined in claim 1 and the claims dependent on that independent claim recite further technical features that are optional, and embodiments that are preferred.

The system provides a pre-tensioner, conveniently a tube, which is actuable, prior to actuation of the implant release means, to set the pre-tensioner in a tensioning disposition in which it imposes on at least a portion of the sheath a tension which pulls the portion in a proximal direction, thereby to reduce the force which the release means must impose on the proximal end of the sheath to initiate the set proximal translation of the sheath to begin said release of said implant.

Thus, it will be appreciated by the reader that the essence of the invention is to provide a "pre-tensioner" at the distal end of the system which somehow "helps" the system components that must pull the stent sheath proximally, from the proximal end of the system. If the pre-tensioner can impose on the sheath a significant force urging the sheath proximally, before the medical practitioner at the proximal end of the system begins to actuate the implant release means, then the burden of stress that must be carried the length of catheter shaft by the implant release means will be reduced by an amount corresponding to the "help" being given to the release means by the pre-tensioner at the distal end of the system.

As will be seen below, the pre-tensioner can perform other functions, besides pre-tensioning. A pre-tensioner in the form of a tube can provide a passage, sealed from the bodily lumen, for transporting a fluid, such as flushing liquid, lengthwise along the catheter. If it takes the place of a pre-existing tubular component for fluid flow, it can simplify the construction of the delivery system even while it improves its performance.

Furthermore, if the pre-tensioner is provided in the form of a tube, that surrounds a core tube of the system that is in endwise compressional stress during release of the stent, then an annulus is provided between the core tube and the pre-tensioner tube that can accommodate a pull wire of the implant release means, within the annulus. In this way, the pre-tensioner tube shields bodily tissue from any contact with the pull wire. The pull wire typically having a very small diameter, it would otherwise have the potential to cause lesions on bodily tissue on the walls of the lumen in which the system has been deployed. Yet further, in a tortuous lumen, when the pull wire is under high endwise tensional stress, there exists the possibility that the tension in the pull wire can cause the core tube to bow outwardly, away from the tensioned pull wire. With a pre-tensioner tube fitting relative snugly around the core tube, and with only a narrow annulus to accommodate the pull wire, the pre-tensioner tube will be very effective in keeping the pull wire close to the core tube and preventing any significant bowing of the core tube away from the tension wire.

In one preferred embodiment, the pre-tensioner tube is of a polymer material that can be pre-tensioned to result in a significant increase of its length, by elastic deformation. Thus, with a polyurethane material PUR it might be possible, for example, to pre-tension it to four or five times its original length in the relaxed disposition, to impose on the stent sheath a substantial proximal pull, before any actuation of the implant release means of the system. In some embodiments, the pull from such a pre-tensioner tube is not enough itself to cause translation of the stent sheath but it is enough to ease the task of the implant release means, when actuated. In other embodiments, the pull from the pre-tensioner is more than enough, in which case there would need to be a component that pushes on the stent sheath, distally, until the time when the stent is to be released. This component could be a push ring bonded to the luminal surface of the stent sheath at its proximal end, or the distal end of the pre-tensioner, and connected to the proximal end of the system by a push rod that can carry an endwise compressional stress until the stent is to be released.

As the stent sheath moves proximally, the strain in the pre-tensioner tube is relieved but, as the deformation is elastic, the pre-tensioner tube simply reverts to a more relaxed disposition, without any significant concertina effect that might otherwise add to the bulk and wall thickness of the tube. This is important because, as noted above, great efforts are being made currently to reduce even further the overall diameter of the shaft of such catheters. Any simplification of shaft structure is interesting for its potential to get overall shaft diameters down even lower.

Polymer deformation is usually time-dependent. Thus, the elastic deformation of a tube pre-tensioner might decay with time, if the tension is imposed in the factory, during manufacture of the system, and prior to transport and lengthy storage of the system prior to use. This invention, therefore envisages embodiments in which the pre-tensioner is of a polymer material that is allowed to remain in its relaxed form until shortly before use of the system, whereupon a manipulation of the proximal end of the system will impose endwise tension on the pre-tensioner and for the first time deliver to the stent sheath a significant proximal pull from the pre-tensioner that will later assist in release of the stent.

The PUR material mentioned above is available from Lubrizol Corporation, Engineered Polymers Division, under the trademark TECOFLEX.

One convenient way of imposing the endwise stress on the pre-tensioner is to couple a proximal end of the pre-tensioner to a tube of the delivery system that extends to the proximal end of the system and offers there a proximal end of the tube that can be pulled proximally (such as just before any part of the stent delivery system comes into contact with the body of the patient) to impose the said axial strain on the pre-tensioner. A bonus effect of this "cocking" process is that it will slightly reduce the wall thickness and diameter of the pre-tensioner tube, as the tube is stretched, all of which can be useful if the distal end of the delivery system is to be advanced along a particularly tortuous or narrow bodily lumen. As explained above, this pre-tension might not be enough to begin the translation of the sheath relative to the stent, but is enough to be of significant help to the stent release means, when the time comes to pull on the sheath to translate it proximally to release the stent into the lumen. Alternatively, the pre-tension might in other embodiments be more than enough so that one has to push on the stent sheath until the implant is to be deployed, to prevent premature deployment. One envisages a combination of a pre-tensioner and an implant release means that can carry both a tensile and a compressive end-to-end stress. Until the implant is released any stress is compressive. When the implant release process begins, however, any end-to-end stress in the implant release means is tensile.

An anchoring means may be provided for anchoring the outer tube of the delivery system that extends to the proximal end of the system and that is coupled to the proximal end of the pre-tensioner to hold the tube in a "cocked" position following the "cocking" process. The anchoring means may involve the outer tube being anchored to the core tube. This may be achieved by providing holes on the outer and core tubes that align upon "cocking" so that a pin can be placed therethrough preventing relative axial movement of the outer tube and core tube.

The description above is of one way to impose a pre-tension on the stent sheath. Other ways will occur to readers. For example, a pre-tensioner component in the form of a helical spring of, say, stainless steel might be thought attractive. Advantageously, such a spring is covered by a film, so that the pre-tensioner can serve as a liquid conduit as explained above. It might be advantageous to use any such film as a pre-tensioner to act with the spring to deliver an aggregate pre-tensioning force. Here, the different stress strain properties of the metal and the polymer could deliver interesting aggregate effects. Other combinations of materials can be used, or composite materials, to deliver the elastic deformation performance required of the pre-tensioner in any given product.

The present invention can be applied to delivery systems in which an implant is radially constrained by a sheath of two co-axial layers. The pre-tensioner pulls the outer of the two sheaths, whereupon the inner of the two sheaths can release the implant.

One such two layer sheath is a so-called rolling membrane, which is a sheath doubled back on itself at its distal end, at the distal end of the implant.

Another such two layer sheath is formed by an inner sheath that has two long edges held together by stitches, that run the full axial length of the implant. Alternatively, the long edges may be held together by stitches that run along a portion of the full axial length of the implant. See WO2010/063795, which is incorporated herein by reference in its entirety. The pre-tensioner provides an outer sheath that covers the inner sheath and the stitches. It is bonded to the inner sheath, or contiguous with the inner sheath around the circumference at the distal end of the inner sheath. It is in endwise tension but the inner sheath is not. On pulling back the thread, the thread releases the stitches one by one, to allow the inner sheath long edges to move away from each other on the circumference of the implant. This release of the stitches enables the pre-tensioner for the first time to pull the distal end of the inner sheath proximally, out of the way of the radially expanding implant, beginning at the distal end and progressing proximally, to the proximal end of the implant.

Other configurations will occur to those skilled in the art. As explained above, an advantage of the invention is that it is no longer necessary to expose the full length of the catheter delivery system to the full endwise force needed to pull the sheath proximally off the stent. With a pre-tensioner near the distal end of the system, some of the high forces needed can be contained in a circuit within the distal end portion of the delivery system, so that less than the full amount of the necessary stress need be delivered to the sheath at the distal end of the system, all the way from where it originates, at the proximal end of the system. The shaft of the system can thus be made less stiff and bulky than might otherwise be the case.

In the case where the pre-tensioner takes the form of a tube located proximal of the sheath, the forces can be contained in the circuit within the distal end portion of the delivery system by employing the aforementioned anchoring means.

Besides, in a rapid exchange catheter system, the absence of telescoping tubes in the catheter shaft proximal of the implant could allow the proximal guidewire lumen exit port to be brought somewhat closer to the distal end of the catheter than might be possible with a telescoping system of tubes. The avoidance of a telescopic arrangement could help to get down to an even lower value the aggregate wall thickness of the catheter system near its distal end, with consequential reduction in outside diameter of the catheter shaft. It is a challenging engineering problem, to achieve near 100% reliability of telescopic sliding, when the telescopic elements have minimal wall thickness. Elimination of telescopic tubes in the catheter shaft, therefore, can reduce the number of challenges facing the designers of systems such as these.

BRIEF DESCRIPTION OF THE DRAWINGS

For a better understanding of the invention, and to show more clearly how the same may be carried into effect, reference will now be made, by way of example, to the accompanying drawings, in which FIGS. 1 to 7 each show a lengthwise section through the longitudinal axis of a stent delivery system. FIGS. 2 to 7 are in accordance with the present invention. Only a distal end zone of the system is shown. Experienced readers will be familiar with the construction and operation of the proximal end of such systems.

FIG. 1 included for the sake of clarity, shows the system without any pre-tensioner.

FIG. 2 shows the system of FIG. 1 but with a pre-tensioner tube added, and in its relaxed disposition.

FIG. 3 shows the system of FIG. 2, and with the pre-tensioner tube in its tensioned disposition.

FIG. 4 shows the system of FIG. 2, with the implant part released into the bodily lumen.

FIGS. 5 to 7 show a second embodiment of implant deliver system in accordance with the invention, in which FIG. 5 shows a storage disposition, FIG. 6 a pre-tensioned disposition and FIG. 7 an implant release disposition.

DETAILED DESCRIPTION

Although the present invention is embodied in an implant delivery system, which does not require the presence of an implant, nevertheless, we show a stent implant 10 in the drawings, in the interests of clarity and so that the reader can better grasp how the system works.

In FIG. 1, the stent 10 is surrounded by a sheath 12 that confines the self-expanding stent radially until the moment of its release into a bodily lumen. In this embodiment, the sheath 12 has a distal end 14 that exhibits an inward taper 16 to provide the leading end of the system with an atraumatic profile. The tip tapers to a core tube 18 of the system which serves as a lumen 20 for a guidewire. On the abluminal surface 22 of the core tube 18 is mounted a stent pusher element 24 which, here, is in the form of a ring, that will restrain the stent 10 from moving proximally during the time when the sheath 12 is being pulled proximally, to release the stent. Other forms of pusher element are known, that are not in the form of a ring, and then can be used in the present invention too. It will be appreciated that the pusher element 24 and the core tube 18 will therefore hold the stent 10 at an axial position in the bodily lumen, exactly where the medical practitioner desires to release the stent 10 into the lumen.

At the proximal end 26 of the sheath 12, on the luminal surface 28 of the sheath, there is provided a pull ring 30 by means of which the sheath 12 can be pulled proximally to release the stent. Attached to the pull ring 30 is the distal end of a pull wire 32 that runs all the way to the proximal end of the system, where it can be put into tension. The tension runs the length of the pull wire 32 and through the pull ring 30 to the sheath 12, to pull the sheath proximally, when required.

Thus, the fundamentals of the illustrated embodiment include a core tube 18 that runs all the way to the proximal end of the system and is in endwise compressive stress during release of the stent, and a pull wire 32, that runs (at least in a distal portion of the system) outside the lumen of the core tube 18 and is in tensional stress when the stent is being released.

Readers will, however, be aware of delivery systems for self-expanding stents in which the stent sheath is connected to the proximal end of the system by a pull tube with a lumen that contains a push rod connected to a component analogous to the pusher ring 24. The present invention is applicable also to such "pull tube" systems.

As mentioned above, other embodiments have a pre-tensioner with more than enough force to pull the implant sheath proximally. In such embodiments one needs a pusher, to push on the pre-tensioner or the stent sheath until the implant is to be released. Then, with a relaxing of this push, the pre-tensioner becomes free to pull the sheath proximally, to release the implant.

In FIG. 1, we show schematically an outer tube 34 that surrounds the core tube 18 and the pull wire 32 and also runs all the way to the proximal end of the system. One can appreciate that there is an axial gap G1 between the distal end 36 of the outer tube 34 and the pull ring 30. In this gap G1, the core tube 18 and pull wire 32 lie side by side. It can be imagined that, when G is big enough and when the tension in pull wire 32 is high enough, there might be some tendency for the core tube 18 to bow outwardly and away from the pull wire 32 in tension. The present Applicant has indeed proposed (see WO2010/115925, which is incorporated herein by reference in its entirety) the use of a plurality of belts at spaced intervals along the length of the gap G1, to prevent any such bowing.

However, with the present invention, as shown in FIGS. 2, 3 and 4 a pre-tensioner tube 40 bridges the gap G, thereby eliminating the need for any of the above-mentioned belts. Nevertheless, we can envisage retaining such belts, inside the pre-tensioner tube.

Comparing FIGS. 1 and 2, it can be seen that the outer tube 34 extends distally in FIG. 2 further than in FIG. 1. Indeed, it will be noted that in FIG. 2 the length of the gap G2 is significantly less than the length of the stent to be deployed. It would appear that the gap G2 is not big enough to allow the sheath to be retracted far enough to release the full length of the stent. However, comparing FIGS. 2 and 3, we see that the outer tube has been pulled back proximally in preparation for use of the delivery system, so that gap G3 is now a multiple of the length of the gap G2 in FIG. 2. The proximal withdrawal of the distal end of the outer tube 34 has imposed considerable elastic deformation on the pre-tensioner tube 40, but that tension has not, of itself, moved the pull ring 30 at all in the proximal direction. Nevertheless, the pull ring 30 is experiencing a proximal pull from the tensioned pre-tensioner tube 40, that will allow the sheath to be translated proximally, relative to the push ring 24, at rather lower levels of endwise tension in the pull wire 32 than would be the case in the absence of the pre-tensioner tube 40.

When the time comes to release the stent, the release process is accomplished in the FIG. 3 system just as in the FIG. 1 system, but is accomplished at a lower level of stress in the pull wire 32 than would be needed in the FIG. 1 embodiment. Furthermore, it can be seen that the abluminal cylindrical surface of the delivery system in the distal end zone is more streamlined in the case of the embodiment in accordance with the present invention, because that abluminal surface lacks any shoulder at the pull ring 30 and the distal end 36 of the outer tube 34. Instead, the pre-tensioner tube eliminates both of these shoulders exposed to the walls of the bodily lumen.

Furthermore, it will be appreciated that the addition of the pre-tensioner tube 40 does not increase at all the number of surfaces in the delivery system that during stent release must slide over each other. On the contrary, by eliminating a telescopic or concertina arrangement, the pre-tensioner tube can reduce the aggregate wall thickness of a distal portion of the delivery system to less than what it would otherwise have been. Although the magnitude of frictional forces that arises, with surfaces sliding over each other, can be managed down to remarkably low levels, nevertheless they remain above zero, so that minimisation of mutually sliding surfaces is a design objective of great interest to high performance catheter type stent delivery systems. Any tendency that telescopically sliding surfaces have to bind against each other and stick, during sliding, is eliminated when the telescopic elements are eliminated from the system.

Although the illustrated embodiment shows a pull wire 32, a pull tube co-axial with core tube 18 can be used.

Although the above description is of a sheath with only one layer, the present invention is applicable to sheaths that are in the form of a two layer membrane, doubled back on itself at its distal end to function during release of the implant as a so-called "rolling membrane". One example is the embodiment of FIGS. 5 to 7.

Turning to the embodiment of FIGS. 5, 6 and 7, FIG. 5 shows the delivery system 100 for a self-expanding stent 102 carried on a catheter shaft tube 104 and confined radially by a rolling membrane sheath 106 that comprises an inner membrane 108 and an outer membrane 110, connected together at the respective distal end 112. The proximal end of the inner membrane 108 is fixed to the shaft 104 at a fixation zone 114. The proximal end of the outer membrane 110 has a pull ring 116 to which is fixed the distal end of a pull wire 118 that runs all the way back to the proximal end of the delivery system. The distal end of the stent 102 is just proximal of an atraumatic tip 120 on the shaft tube 104, with the usual distal guidewire exit port 122 on the axis of the tip 120. The proximal end of the stent 102 butts up against a stop ring 124 also fixed to the shaft 104.

Thus far, the arrangement described is that of a "conventional" rolling membrane release system for a self-expanding stent. By pulling on the pull wire 118, the membrane is caused to roll back proximally on itself, gradually to release the self-expanding stent, distal end first. However, the embodiment of FIG. 5 reveals a variant, in that the inner membrane 108 is of the form described in Applicant's earlier WO2010/063795 mentioned above, with two long edges held together by stitches. The stitches are shown schematically in FIG. 5 as short branches 130 on a thread 132 that runs all the way to the proximal end of the catheter delivery system. Upon pulling the thread 132 proximally, the stitches 130 are released, one at a time, commencing at the distal end of the inner sheath 108, that is to say, that the distal end of the self-expanding stent 102. It will be appreciated that, with the stitches 130 all intact, the stent 102 is confined radially by the inner membrane 108 and outer membrane 110 of the rolling membrane 106.

Turning now to FIG. 6, attention is directed to the pull ring 116 on the outer membrane 110. The pull wire 118 has been used to pull the pull ring 116 to a position well proximal of its location in the FIG. 5 storage disposition. However, the distal end of the outer membrane 110 has not moved proximally. The elastic deformation of the outer membrane 110 generates a pull on the distal end of the inner membrane 108 which is not sufficient, for as long as the stitches 130 remain intact, to permit the distal end of the inner membrane 108 to invert on itself and roll proximally down the abluminal surface of more proximal parts of the inner membrane 108.

However, looking at FIG. 7, as soon as the thread 132 through the stitches 130 is pulled proximally, the stitches will open, one by one, commencing at the distal end of the system next to the tip 120. This opening of the distal stitches releases the hoop stress around the circumference of the inner membrane 108 at its distal end, and this has the further consequence of allowing the tensioned outer sheath 110 to invert the distal end of the inner membrane 108 and pull it back proximally, outside that proximal portion of the length of the inner membrane 108 where the stitches are still in tact. It will be appreciated that the tension in the outer membrane 118 helps to pull the rolling membrane, both inner membrane 108 and outer membrane 110, proximally clear of the radially expanding stent 102, with most or all of the rolling membrane, at the end of the stent release process, pulled to a position proximal of the fixation zone 114 at the proximal end of the inner membrane 108. An advantage of this proximal movement is a reduced likelihood of any part of the rolling membrane ending up being squeezed between the radially expanded stent 102 and the stenosed bodily lumen in which the stent has been placed. This proximal pulling of the rolling membrane, away from the stenting site, is a routine feature of a rolling membrane release system, but not of a delivery system in which stent release is effected simply by release of a line of stitches along the length of a sheath confining a self-expanding stent. The combination of a line of stitches, a rolling membrane, and a pre-tensioning facility opens up possibilities for the designer of catheters for delivery of implants into a bodily lumen that are unavailable in other system architectures.

Although the illustrated embodiment shows an "over the wire" system, readers will be able to adapt the inventive concept to rapid exchange systems which exhibit a guidewire lumen confined to a distal portion of the length of the catheter of the system. As mentioned above, the pre-tensioner tube can open up possibilities to get the proximal guidewire exit port closer to the distal end of the delivery system.

Devices manufactured for use later have a "shelf life" over which they can be stored and, afterwards, still used safely. While it is assumed above that the pre-tensioning will be done after the storage period and before use, it is also imagined that pre-tensioning might be feasible as part of the manufacturing process, even before the storage period on the "shelf" even starts.

The catheter system of the present invention may be incorporated with a device for catheter sheath retraction, such as that disclosed in WO 2009/007432 A1, which is incorporated herein by reference in its entirety. Such a device may incorporate a housing connectable to the proximal end of the catheter system and a mover associated with the housing for actuating the catheter system via the actuating means of the catheter system.

Thus, the storage disposition, where the pre-tensioner takes the form of a tube located proximal of the sheath, may take the form depicted in either of FIG. 2 or 3. Where the pre-tensioner takes the form of an outer sheath, the storage disposition may take the form depicted in either of FIG. 5 or 6.

The present invention may have application to catheters other than those for delivery of an implant. The pre-tensioner can be useful whenever a load is to be transmitted from an accessible proximal end of the catheter outside the body to the distal end of the catheter, in the body, inaccessible and perhaps separated from the proximal end by a bodily lumen that is long and/or tortuous. A pre-tensioner near the distal end can reduce the load and this alone can open up design possibilities that would otherwise be precluded.

The invention claimed is:

1. A transluminal catheter system to deliver a bodily implant, the system comprising: a proximal end with an implant release and a distal end that carries the implant radially confined within an inner sheath which, to release the implant, is pulled proximally from the proximal end of the system by the release to translate the inner sheath proximally relative to the implant to release the implant from its radial confinement, progressively, starting at the distal end of the implant; and a pre-tensioner which is actuable, prior to actuation of the implant release, to set the pre-tensioner in a tensioning disposition in which it imposes on at least a portion of the inner sheath a tension which pulls the portion in a proximal direction, thereby to reduce the force which the release must impose on the proximal end of the inner sheath to initiate said proximal translation of the inner sheath to begin said release of said implant, wherein the pre-tensioner takes the form of an outer sheath that covers said inner sheath, wherein said inner sheath has two long edges held together by stitches that run lengthwise along the implant, the pre-tensioner bonded to the inner sheath, or contiguous with the inner sheath around the circumference at the distal end of the inner sheath, and the pre-tensioner arranged to be put into end-wise tension, whilst the inner sheath is not in end-wise tension.

2. The system according to claim 1, wherein the stitches run the full axial length of the implant.

3. The system according to claim 1, wherein the implant is a stent.

4. The system according to claim 3, wherein the stent is a self-expanding stent.

5. The system according to claim 1, wherein the system is an over a wire system.

6. The system according to claim 1, wherein the system is a rapid exchange system.

7. The system according to claim 1, wherein the implant is radially confined within the inner sheath.

\* \* \* \* \*